US008663285B2

(12) United States Patent
Dall et al.

(10) Patent No.: US 8,663,285 B2
(45) Date of Patent: Mar. 4, 2014

(54) EXPANSION DEVICES

(75) Inventors: Vagn-Erik Dall, Langley (GB); Cody Eric Bunger, Auning (DK)

(73) Assignee: Dalmatic Lystrup A/S, Lystrup (DK)

( * ) Notice: Subject to any disclaimer, the term of this patent is extended or adjusted under 35 U.S.C. 154(b) by 84 days.

(21) Appl. No.: 13/394,054

(22) PCT Filed: Sep. 3, 2010

(86) PCT No.: PCT/GB2010/001678
§ 371 (c)(1),
(2), (4) Date: May 23, 2012

(87) PCT Pub. No.: WO2011/027126
PCT Pub. Date: Mar. 10, 2011

(65) Prior Publication Data
US 2012/0245636 A1 Sep. 27, 2012

(30) Foreign Application Priority Data
Sep. 3, 2009 (GB) .................................. 0915382.6

(51) Int. Cl.
*A61B 17/70* (2006.01)
*A61B 17/88* (2006.01)

(52) U.S. Cl.
USPC ............................ 606/258; 606/259; 606/105

(58) Field of Classification Search
CPC ................................ A61B 17/70; A61B 17/88
USPC ............. 606/57, 58, 246, 257, 258, 264, 279, 606/63, 68, 320, 326, 90, 105; 251/12, 251/61.1, 129.01, 335.3
See application file for complete search history.

(56) References Cited

U.S. PATENT DOCUMENTS

| 4,502,473 A * | 3/1985 | Harris et al. ..................... 606/58 |
| 5,626,581 A * | 5/1997 | Staehlin et al. .................. 606/63 |
| 2006/0047282 A1 | 3/2006 | Gordon | |

* cited by examiner

*Primary Examiner* — Pedro Philogene
*Assistant Examiner* — David Comstock
(74) *Attorney, Agent, or Firm* — Katherine H. McGuire, Esq.; Woods Oviatt Gilman, LLP

(57) ABSTRACT

An expansion device is disclosed which, when mounted on an appropriate support, can make controlled advancement relative to the support in response to activation from a remote site. The device comprises first (6) and second (8) elements coupled for relative movement along an axis defined on a support 2. An expandable chamber is defined between the elements, in which chamber is a flexible and elastic membrane (24). A resilient mechanism urges the two elements towards each other to define a minimum volume for the chamber. The chamber can be expanded to separate the elements, and hold mechanisms typically in the form of latches, are provided for selectively restricting movement on the respective elements relative to the support. Thus, activation of the expansion means advances the first element relative to the second element while the second element is held relative to the support, and subsequent deactivation of the expansion mechanism allows the resilient mechanism to advance the second element relative to the support and the first element, and to contract the chamber, while the first element is held relative to the support. Devices of the invention have particular application in the control of the growth of a bone or a bone structure, especially in the context of spinal surgery.

26 Claims, 5 Drawing Sheets

EXPANSION DEVICES

This invention relates to expansion devices, and particularly to devices for use in orthopaedic surgery for controlling the growth of bone or bone structures. The invention has particular application in the control of the spinal curvature, either to correct excessive curvature or maintain a correct or corrected curvature in a distorted spinal structure. Reference is directed to co-pending International Patent Publication Nos: WO/2010/052462 and WO/2010/052465, incorporated herein by reference, directed respectively at Bone Fixation Devices and Bone Fixation Systems for use in spinal surgery.

The most common method in current use for preserving or extending the length of bones or bone structure is to couple external fixation systems with some form of lengthening mechanism, or to use an intra-medular device with an electric motor for extending it. The lengthening or extending mechanisms are normally conducted on an occasional basis, and in accordance with medical and surgical advice. Examples of bone elongation or lengthening devices are disclosed in British Patent Specification No: 1 507 913 and U.S. Pat. No. 5,626,581, incorporated by reference.

The present invention is directed at an expansion device which, when mounted on an appropriate support, can make controlled advancement relative to the support in response to activation from a remote site. Such a device can be useful in lengthening or extending mechanisms of the type referred to above. According to the invention the device comprises first and second elements coupled for relative movement along an axis typically defined on a support. The device itself defines an expandable chamber between opposed walls respectively on the first and second elements, with a resilient mechanism urging the opposed walls towards one another. Means are provided for expanding the chamber to move the opposed walls away from one another against the force of the resilient mechanism, and hold mechanisms typically in the form of latch members, are provided for selectively restricting movement of the respective elements on the axes relative to such a support. Activation of the expansion means advances the first element along the axis relative to the second element while the second element is held relative to the support. Deactivation of the expansion means allows the resilient mechanism to advance the second element along the axis relative to the support and the first element and to contract the chamber, while the first element is held relative to the support. In most embodiments of the invention the chamber will have a minimum volume to which it returns upon deactivation of the expansion means.

In most embodiments of the invention, the expandable chamber is defined between the base of a normally circular recess formed in one of the two elements, and the end of the other element received therein. Normally, each of the elements, the recess and the expandable chamber has a circular cross-section and most conveniently, each of these circular cross-sections will be symmetrical about the movement axis.

The expansion means will typically comprise an expandable membrane in the chamber enclosing a fluid. While the membrane can be expanded by pumping fluid into the enclosed volume, in the practice of the invention it is preferred to confine a sealed mass of fluid within the membrane and expand the chamber by heating the fluid to swell the membrane against the opposed walls of the chamber. This can be accomplished by means of an electric heating coil within the body of fluid, and connected to a source of electrical power which, in preferred embodiments, is a rechargeable battery, via a suitable switch or control mechanism. Charging the battery can be accomplished from an induction coil, via appropriate micro circuitry. The circuitry which will normally include a reed switch as well as a printed circuit board, controls the level to which the battery is charged when the induction coil is exposed to an alternating magnetic field.

It will be appreciated that when used in post-surgical treatment, the device of the invention, the battery, the micro circuitry and the induction coil can all be permanently connected, and in some cases, installed entirely within a patient under treatment. When it is desired to activate the device of the invention, the patient is appropriately exposed to an alternating magnetic field proximate the induction coil, generating a charge in the coil which is transferred to the battery via the micro circuitry, and then discharged to the heating coil in the expansion device. A transcutaneous energy transfer device suitable for use in devices of the present invention is disclosed in U.S. Pat. No. 5,350,413, incorporated by reference.

The fluid sealed within the membrane or balloon, is preferably water. While other fluids can be used, water is preferred for simple safety reasons. In the unlikely event that the membrane breaks, the leakage of water is unlikely to cause serious damage. The water used would of course be distilled. Water has consistent and predictable expansion characteristics with temperature but, as will be described below, consistency will only be required over a relatively small temperature range as when the expansion cycle is repeated, it will be followed at the same or similar temperature or temperatures on each occasion.

The most simple form of resilient mechanism for urging the opposed walls in a device according to the invention towards each other is a simple spring such as a helical spring. As the elements of the device can readily be mounted on a shaft aligned with the movement axis, a helical spring can easily be mounted on the shaft. As it is preferred that the elements of the device are telescopically engaged piston and cylinder elements, the elements can be combined with a shaft and spring as described above in what is essentially an axial assembly.

As noted above, a device according to the invention is adapted to be used in association with a support, and the respective advancements are defined relative thereto. Thus, in an embodiment of the invention mounted on a support, latch members are disposed on the respective elements and resiliently urged into engagement with a rack on the support. This engagement permits movement of the respective elements along the axis only in the direction of advancement. This can be readily accomplished by designing the rack with a sawtooth cross-section, inclined in the direction of advancement.

As an alternative means of controlling the advance of the device along the support separately operable brake mechanisms can be fitted to the respective elements. Such mechanisms can be operated to lock the second element as the chamber expands to advance the first element, and lock the first element as the chamber contracts to advance the second element.

In most applications of the invention, the device is mounted on a support, which also supports an extension member. The extension member is in engagement with the device whereby advancement of the first element advances the extension member relative to the support. The support and extension member can be a piston-cylinder type construction with the extension member in the form of a rod projecting from the end of the cylinder. In this way, upon each activation and deactivation cycle of the expansion means, the combined length of the support and extension member is increased by the same incremental amount.

As noted above, the invention has particular application in controlling the growth of bones or bone structures. Systems for use in such applications may comprise a device according to the invention in which at least one of the elements is adapted to be coupled to a bone part. Means are then provided for activating the expansion means in accordance with control requirements. These may be manual or automatic, depending upon the nature of the control required.

When used for correcting the curvature of the spine, a device of the invention in combination with the support and an extension member as described above, is fitted surgically by attaching the distal ends of the support and the extension member to vertebra spaced from one another. When used for maintaining curvature of the spine as it grows, such a device is installed with the distal end of one of the support and extension member attached to a central vertebra, with the other being attached to a component extending between remote vertebrae on either side of the control of the central vertebra.

Further features and advantages of the invention will be apparent from the following description of preferred embodiments, in which reference will be made to the accompanying schematic drawings wherein.

Figure 1:
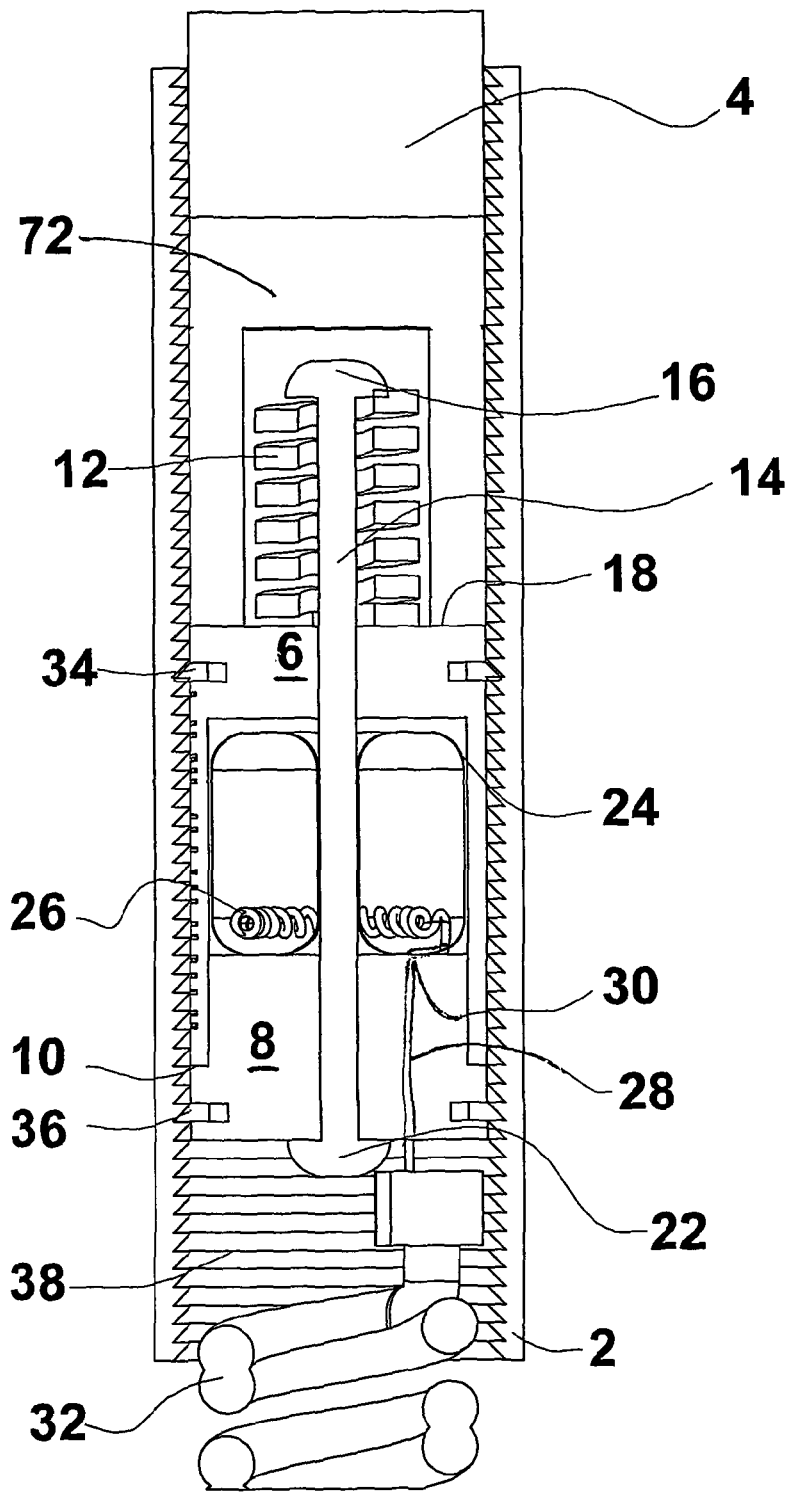
FIG. 1 is cross-section through a device according to a first embodiment of the invention installed in a support with an extension member.

FIG. 1 shows a device according to the invention installed within a support 2, with an extension member 4. The device itself comprises first (6) and second (8) elements. The first element 6 is cylindrical at its end facing the second element 8 to form a circular recess, in which the main body of the second element 8 is received. The second element 8 does though, form a shoulder 10 against which the rim of the recess of the first element 6 will normally rest. The elements are held in this "rest" position by a helical spring 12 on a shaft 14, both of which extend on the axis of the support 2, the spring being held between the head 16 of the shaft and the exposed face 18 of the second element, and the shaft 12 extending through both elements and being held against the outer face 20 of the first element 8 by boss 22.

As can be seen, the first and second elements 6, 8 define a chamber between them, through which the shaft 12 extends. This chamber is lined by a flexible and elastic membrane 24, within which is sealed a quantity of fluid, normally water. The membrane is in the form of an annulus extending around the shaft 12. Within the annulus is a heating coil 26. This is connected by wiring 28 extending through a part of the membrane wall sealed to the element 8 at 30 and along spiral cord 32 to a source of electric power as described below.

The elements 6, 8 of the illustrated device are located in the support 2 by means of latch mechanisms consisting of piston rings, normally split rings 34,36 mounted respectively on the first and second elements, and engaging a rack 38 formed on the internal surface of the support 2. The rack 38 has the cross-section of an inclined saw tooth. The respective piston rings 34 and 36 have complementary cross-sections and are able to retract into their support grooves. In this way both elements of the device can be forced, to the right as shown in FIG. 1, over the saw teeth of the rack 38, but not in the opposite direction.

When electric power is delivered to the heating coil 26, the mass of fluid, normally water, confined in the membrane expands to increase the size of the chamber in the only way possible; ie, by separating the elements 6 and 8. This can only be accomplished in one direction; vertically upwards as shown, because of the engagement of the ring 36 with the rack 38, and accordingly the element 6 advances away from the element 8, forcing the piston ring 34 over the saw teeth of the rack 38 by an amount dependent upon the expansion of the membrane fluid, which itself is determined by the increase in temperature achieved by the heating coil 26. Typically the amount of movement will be around 0.5 millimeter, but of necessity in the embodiment shown, by an amount determined by the pitch of the saw teeth in the rack.

Once the desired advancement of the element 6 has been accomplished, the heating coil is disconnected and the fluid within the membrane cools. As it does, the expanded annulus contracts, and the spring 12 draws the second element 8 back into its rest position, with the shoulder 10 engaging the rim of the first element 6. It will be appreciated that in doing so the second element 8 will have advanced by a distance corresponding to the same number of teeth on the rack 38 as the first element 6 and thus the device as a whole will have moved that specified distance along the support, and in doing so advanced the extension member 4 the same distance.

An equaliser 72 is disposed between the extension member 4 and the element 6 to control the advance of the member 4 in response to activation of the device. Initial separation of the elements 6 and 8 compresses the spring 12 while leaving the shaft 14 in place. This movement compresses the equaliser 72 around the spring 12, and as it subsequently expands to its normal shape, the extension member is moved, upwards as shown, a corresponding amount. The equaliser 72 thus ensures that there is no sudden movement of the extension member 4. When the membrane 24 is subsequently allowed to collapse, and the spring 12 draws the element 8 to its position relative to element 6 as shown in FIG. 1, there is preferably no direct engagement between the head 16 of the shaft 14 and the equaliser 72. However, the resilient nature of the equaliser ensures that in the event of such contact being made, there is no sudden movement of the extension member 4.

Figure 2:
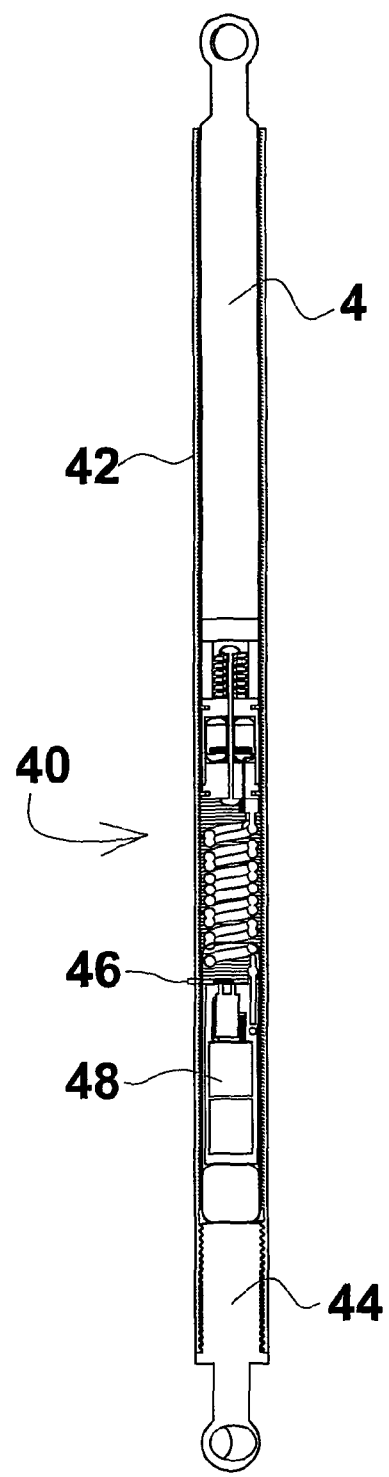
FIG. 2 illustrates the device of FIG. 1 as part of an extendible unit.

FIG. 2 illustrates how the device of FIG. 1 may be installed in an extendible unit. The device itself, indicated at 40 is confined in a tube 42 along at least part of the internal wall thereof which forms the rack 38. It will be appreciated that the teeth of the rack need not extend around the full inner circumference or along the full length of the tube, but may be in the form of separate elongate sections, and only in the length of tube 42 along which the device is to move. At one end of the tube is fixed a boss 44. The other end receives the extension member 4 of the device. A terminal 46 projects from the tube 42 for connection to a source of electrical power. A control unit 48 housing the electrical system for the heating coil 26, is installed within the tube 42 and controls the transmission of power from the source to the device, and to the heating coil 26.

Figure 3:
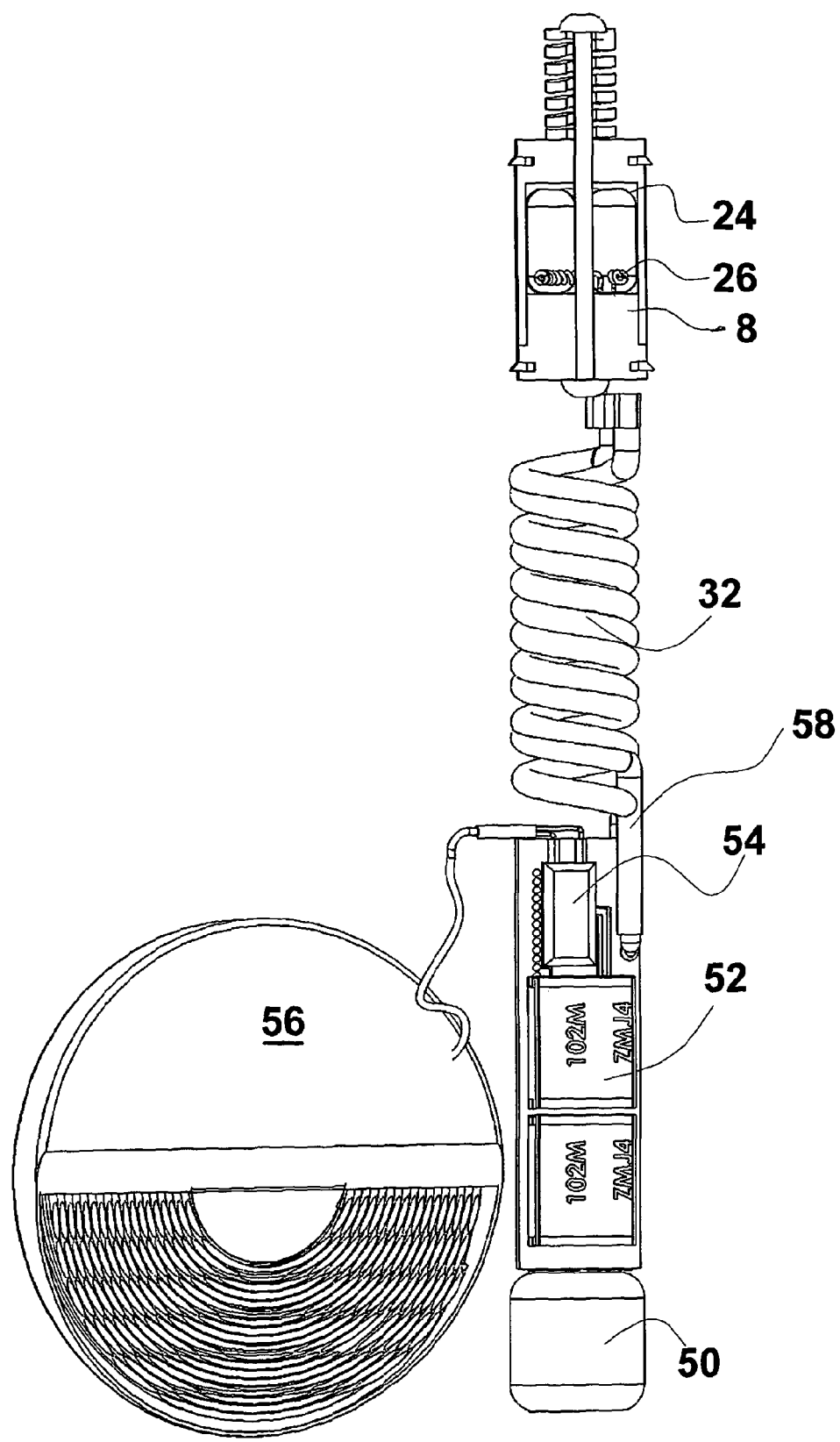
FIG. 3 shows the components in a device according to the invention, and means for activating it.

FIG. 3 shows the electrical system for energising the heating coil 26 in the device of FIG. 1. Its essential components are the battery 50; the circuit board indicated at 52; the reed switch 54, and the induction coil 56. The battery 50 is rechargeable, to a pre-set level. It is coupled via the circuit board 52 and reed switch 54 to the induction coil 56, to receive charge from the induction coil 56 when it is exposed to an alternating magnetic field. The reed switch sets the level of charge, and when the battery is charged to that level, it is permitted to discharge to the heating coil 26. The battery is connected to the heating coil by wires which extend through a boss 58 coupled to the support 2 and along the spiral cord 32 within the support 2 to the internal wiring 28 within the second element 8 to the coil 26 within the annular membrane 24. The entire assembly, excluding the induction coil 56, can be contained in a cylindrical space of around 6 mm diameter and around 6 cm long; about the size of a cigarette. It can therefore be installed in a unit of the kind indicated in FIG. 2, to be incorporated in a bone fixation or alignment system as described below.

Figure 4:
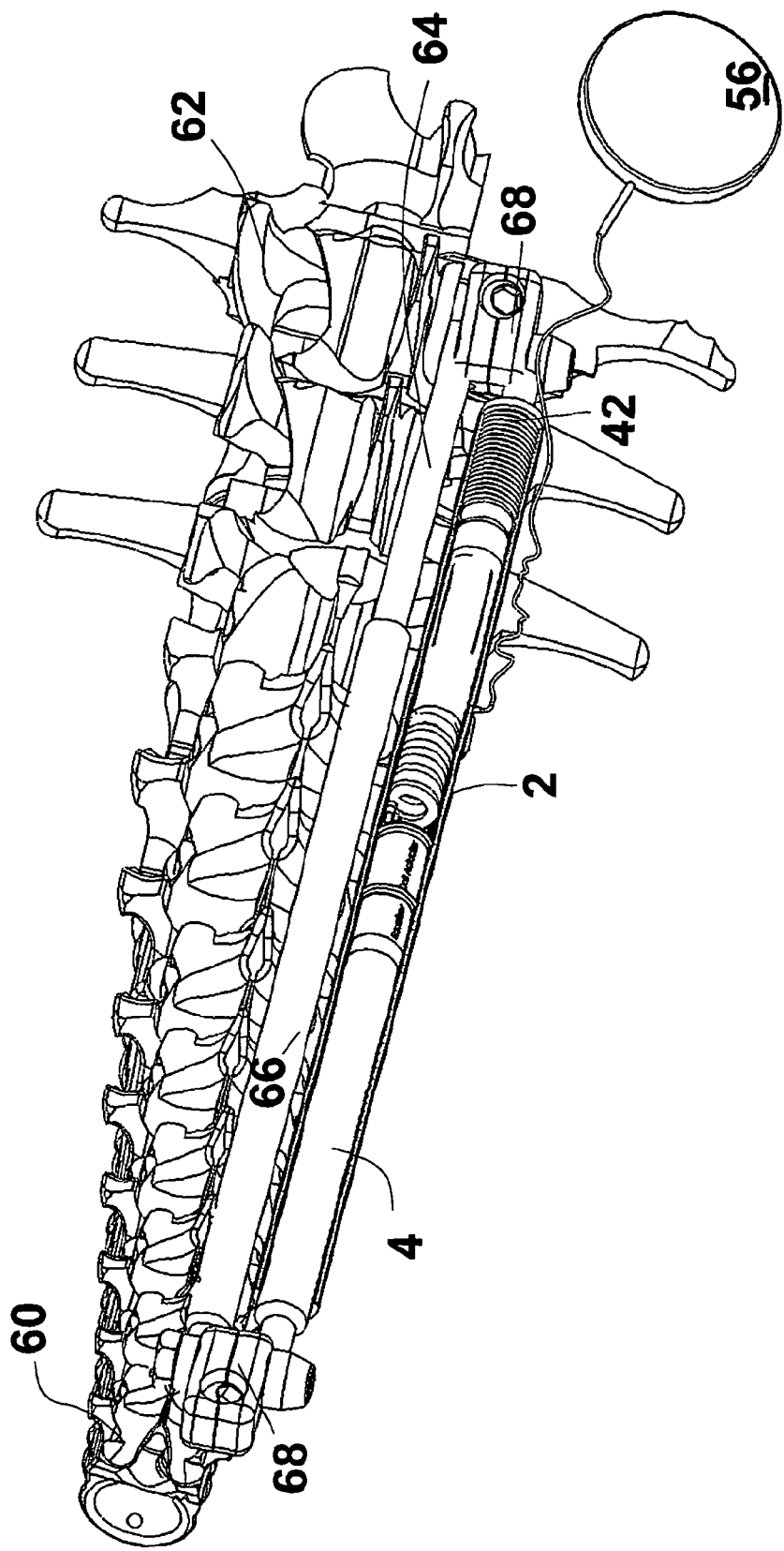
FIG. 4 illustrates how an embodiment of the device according to the invention can be used in spinal surgery.
Figure 5:
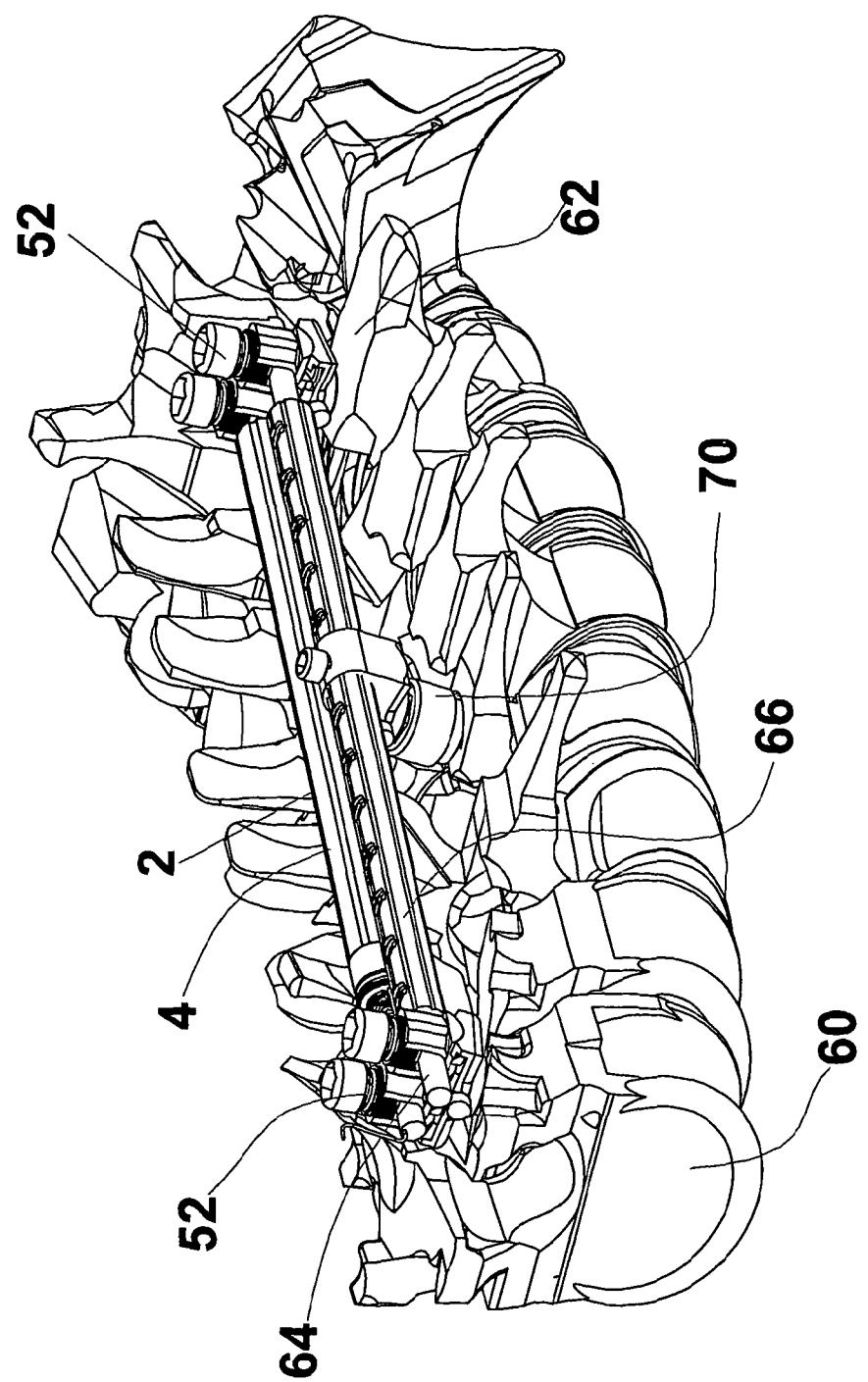
FIG. 5 shows a device according to the invention can be used in a different way in spinal surgery.

FIGS. 4 and 5 show how devices according to the invention can be used in a bone fixation or alignment system applied to a spinal section. A fixation device of the kind described in International Patent Specification No: WO/2010/052462, referred to above, is mounted in each of two remote vertebra 60, 62. Each such device is adapted to receive two fixation rods. One is a plain rod 64 with a reinforcement sleeve 66. The other comprises a support 2 and an extension member 4 as described above. The rod 64 is slidingly received on the housing of the respective fixation devices. The support 2 and extension member 4 are locked in or at least held against clamps on the respective fixation devices. The boss 42 of the support 2 will normally be locked in a clamp 68, as shown in FIG. 4. As can be seen, the components of the expansion device according to the invention are located proximate the clamp 68 on the fixation device mounted in vertebra 60.

A second device according to the invention is illustrated in FIG. 5 at 70. The device 70 is mounted on a pedical screw (not shown) installed in a central vertebra between remote vertebra 60 and 62, and oriented generally perpendicular to the fixation rod 64 and the combined support 2 and extension member 4. The device 70 operates in essentially the same way as that described above, to preserve and extend the distance between the central vertebra and the fixation rod 64. This is accomplished by coupling the device between the central vertebra and a union block which will normally be slidably mounted on the reinforcement sleeve 66 of the rod 64. The device can be used to preserve a desired degree of curvature in the spine between the remote vertebra 60,62. The spacing between the remote vertebra 60, 62 extends as the spine grows, and also as a consequence of the expansion device fitted between the support and extension member aligned with the fixation rod 64. The rod 64 and extension member 4 preserve the alignment of the remote vertebra; the expansion device coupled to the extension member provides controlled extension of the spacing between the remote vertebra. As and when it is required to increase the curvature of the spine between the remote vertebra, the device 70 can be activated in the manner described above to extend the spacing between the central vertebra and the mid point of the rod 64 and sleeve 66. Similar electronic circuitry as described above can of course be used to activate the device 70, but the parameters must of course be different to ensure that one of the devices is not unintentionally activated as a consequence of the induction coil of the other device being exposed to an alternating magnetic field.

When a system of the kind illustrated in FIG. 5 is installed in a patient, the expansion devices can be selectively activated by applying an appropriate alternating magnetic field to the respective induction coil using a transcutaneous energy transfer device as described above, or of the kind described in U.S. Pat. No. 5,350,413. In other words, no further invasive surgery is required to extend the spacing between remote vertebra in the spine or indeed, to preserve or increase the curvature of the spine between such remote vertebra.

The elements of the expansion device, and the support and extension member will normally be made of a metal such as stainless steel or titanium as are used in medical devices. The flexible/elastic membrane is typically formed in rubber or polyurethane. Whatever materials are used, they must of course be compatible with the respective patient.

Although described particularly with reference to surgical uses, it will be appreciated that the invention can be used in many different fields of industry. For example, it can be used in manufacturing and in space exploration, where a special benefit could be its remote stimulation; ie, without direct manual involvement.

The invention claimed is:

1. An expansion device comprising first and second elements coupled for relative movement along an axis and defining an expandable chamber between opposed walls respectively on the first and second elements; a resilient mechanism for urging the opposed walls towards one another; expansion means for expanding the chamber to move the opposed walls away from one another against the force of the resilient mechanism; and hold mechanisms for selectively restricting movement of the respective elements on said axis relative to a support, whereby activation of the expansion means advances the first element along said axis relative to the second element and a said support, and deactivation of the expansion means allows the resilient mechanism to advance the second element along said axis relative to a said support and the first element and contract the chamber.

2. A device according to claim 1 wherein the chamber has a minimum volume to which it returns upon deactivation of the expansion means.

3. A device according to claim 1 wherein the chamber is defined between the base of a recess formed in one of the first and second elements and the end of the other of the elements received therein.

4. A device according to claim 3 wherein each of the elements, the recess and the expandable chamber has a circular cross-section.

5. A device according to claim 4 wherein each of said circular cross-sections is symmetrical about said axis.

6. A device according to claim 1 wherein the expansion means comprises an expandable membrane in the chamber enclosing a fluid.

7. A device according to claim 6 wherein the membrane confines a sealed mass of fluid, the expansion means including means for heating the fluid to increase its volume and thereby expand the chamber.

8. A device according to claim 7 wherein the heating means is an electric heating coil confined by the membrane and includes connections to a source of electric power.

9. A device according to claim 8 wherein the power source is a rechargeable battery.

10. A device according to claim 9 including an induction coil for recharging the battery.

11. A device according to claim 6 wherein the fluid is water.

12. A device according to claim 1 wherein the resilient mechanism is an helical spring.

13. A device according to claim 1 wherein the elements are mounted on a shaft aligned with said axis.

14. A device according to claim 13 wherein the spring is mounted on the shaft.

15. A device according to claim 1 wherein the elements are telescopically engaged piston elements.

16. A device according to claim 1 mounted on a support, wherein the hold mechanisms are disposed on the respective elements and selectively urged into engagement with the support, which engagement permits movement of the respective elements along said axis only in the direction of said advancement.

17. A device according to claim 16 wherein the hold mechanisms comprise latch members resiliently urged into engagement with a rack on the support.

18. A device according to claim 17 wherein the rack has a saw tooth cross-section inclined in the direction of said advancement.

19. A device according to claim 16 wherein an extension member is mounted on the support and in engagement with the device, whereby said advancement of the first element advances the extension member relative to the support.

20. A device according to claim 19 wherein the support is cylindrical, and the extension member is a rod projecting from an end of the cylinder.

21. A device according to claim 1 wherein activation of the expansion means advances the first element a predetermined distance and deactivation of the expansion means causes advancement of the second element by the same predetermined distance.

22. A system for controlling the growth of bones or bone structures comprising a device having first and second elements coupled for relative movement along an axis and defining an expandable chamber between opposed walls respectively on the first and second elements; a resilient mechanism for urging the opposed walls towards one another; expansion means for expanding the chamber to move the opposed walls away from one another against the force of the resilient mechanism; and hold mechanisms for selectively restricting movement of the respective elements on said axis relative to a support, whereby activation of the expansion means advances the first element along said axis relative to the second element and a said support, and deactivation of the expansion means allows the resilient mechanism to advance the second element along said axis relative to a said support and the first element and contract the chamber, and wherein at least one of the first and second elements is adapted to be coupled to a bone part and means for activating the expansion means in accordance with control requirements.

23. A system according to claim 22 for use in correcting the curvature of the spine, comprising a device according to claim 19 or claim 20; means for attaching the distal ends of the support and the extension member to vertebrae spaced from one another.

24. A system according to claim 22 for use in maintaining curvature of the spine, wherein the device has an extension member mounted on the support and in engagement with the device, whereby said advancement of the first element advances the extension member relative to the support, and includes means for attaching the distal end of one of the support and extension member to a central vertebra and means for attaching the other of the support and extension member to a component extending between remote vertebrae on either side of the central vertebra.

25. A method of controlling the growth of a spinal bone structure comprising installing a system for controlling the growth of bones or bone structures comprising a device comprising first and second elements coupled for relative movement along an axis and defining an expandable chamber between opposed walls respectively on the first and second elements; a resilient mechanism for urging the opposed walls towards one another; expansion means for expanding the chamber to move the opposed walls away from one another against the force of the resilient mechanism; and hold mechanisms for selectively restricting movement of the respective elements on said axis relative to a support, whereby activation of the expansion means advances the first element along said axis relative to the second element and a said support, and deactivation of the expansion means allows the resilient mechanism to advance the second element along said axis relative to a said support and the first element and contract the chamber, and wherein at least one of the first and second elements is adapted to be coupled to a bone part and means for activating the expansion means in accordance with control requirements, and activating the expansion means to extend the spacing between the respective spaced vertebrae.

26. A method of correcting the curvature of the spine comprising installing a system comprising a device having first and second elements coupled for relative movement along an axis and defining an expandable chamber between opposed walls respectively on the first and second elements; a resilient mechanism for urging the opposed walls towards one another; expansion means for expanding the chamber to move the opposed walls away from one another against the force of the resilient mechanism; and hold mechanisms for selectively restricting movement of the respective elements on said axis relative to a support, whereby activation of the expansion means advances the first element along said axis relative to the second element and a said support, and deactivation of the expansion means allows the resilient mechanism to advance the second element along said axis relative to a said support and the first element and contract the chamber, and wherein at least one of the first and second elements is adapted to be coupled to a bone part and means for activating the expansion means in accordance with control requirements wherein the device has an extension member mounted on the support and in engagement with the device, whereby said advancement of the first element advances the extension member relative to the support, and includes means for attaching the distal end of one of the support and extension member to a central vertebra and means for attaching the other of the support and extension member to a component extending between remote vertebrae on either side of the central vertebra, and activating the expansion means to extend the spacing between the central vertebra and the component extending between the remote vertebrae.

* * * * *